United States Patent
Takayama et al.

(10) Patent No.: US 10,217,246 B2
(45) Date of Patent: Feb. 26, 2019

(54) X-RAY COMPUTED TOMOGRAPHY APPARATUS AND CONTROL METHOD

(71) Applicant: Toshiba Medical Systems Corporation, Otawara-shi (JP)

(72) Inventors: Takuzo Takayama, Utsunomiya (JP); Yasuo Saito, Nasushiobara (JP); Emi Tamura, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 364 days.

(21) Appl. No.: 14/747,283

(22) Filed: Jun. 23, 2015

(65) Prior Publication Data

US 2015/0287221 A1 Oct. 8, 2015

Related U.S. Application Data

(63) Continuation of application No. PCT/JP2013/085146, filed on Dec. 27, 2013.

(30) Foreign Application Priority Data

Dec. 28, 2012 (JP) .................................. 2012-288495

(51) Int. Cl.
*G06K 9/00* (2006.01)
*G06T 11/00* (2006.01)
(Continued)

(52) U.S. Cl.
CPC ............ *G06T 11/003* (2013.01); *A61B 6/032* (2013.01); *A61B 6/4241* (2013.01); *A61B 6/482* (2013.01);
(Continued)

(58) Field of Classification Search
CPC ................. G06T 11/003; G06T 11/005; G06T 2211/408; G06T 2211/412; A61B 6/032;
(Continued)

(56) References Cited

U.S. PATENT DOCUMENTS

| | | | | | |
|---|---|---|---|---|---|
| 5,570,403 | A | * | 10/1996 | Yamazaki | A61B 6/032 378/19 |
| 7,260,171 | B1 | * | 8/2007 | Arenson | A61B 6/032 378/16 |
| 2008/0260094 | A1 | * | 10/2008 | Carmi | A61B 6/032 378/19 |
| 2013/0010921 | A1 | * | 1/2013 | Sagoh | A61B 6/032 378/19 |
| 2016/0095561 | A1 | * | 4/2016 | Tamura | A61B 6/032 378/62 |

FOREIGN PATENT DOCUMENTS

| | | |
|---|---|---|
| JP | 2000-189409 A | 7/2000 |
| JP | 2010-243395 A | 10/2010 |

(Continued)

OTHER PUBLICATIONS

Written Opinion dated Apr. 1, 2014 in PCT/JP2013/085146 filed Dec. 27, 2013 with English translation.

(Continued)

*Primary Examiner* — Vincent Rudolph
*Assistant Examiner* — Timothy Choi
(74) *Attorney, Agent, or Firm* — Oblon, McClelland, Maier & Neustadt, L.L.P.

(57) ABSTRACT

An X-ray computed tomography (CT) apparatus includes a detector, and processing circuitry. The detector is configured to output, at each incidence of an X-ray photon, a signal enabling measurement of an energy value of the X-ray photon. Processing circuitry is configured to estimate an energy range to be used for imaging based on an imaging condition and to reconstruct X-ray CT image data using counting information to which an energy value within the energy range is associated among pieces of counting information that are collected from individual signals output by the detector at each incidence of an X-ray photon that has been irradiated from an X-ray tube and has passed through (Continued)

a subject, and in which a counting value and an energy value of X-ray photons incident to the detector are associated with each other.

8 Claims, 10 Drawing Sheets

(51) Int. Cl.
*A61B 6/03* (2006.01)
*A61B 6/00* (2006.01)
*G01N 23/046* (2018.01)
*G01T 1/16* (2006.01)
*H05G 1/08* (2006.01)

(52) U.S. Cl.
CPC ......... *G01N 23/046* (2013.01); *G01T 1/1606* (2013.01); *G06T 11/005* (2013.01); *H05G 1/08* (2013.01); *A61B 6/4035* (2013.01); *A61B 6/4233* (2013.01); *G06T 2211/408* (2013.01); *G06T 2211/412* (2013.01)

(58) Field of Classification Search
CPC ..... A61B 6/4241; A61B 6/482; A61B 6/4035; A61B 6/4233; G01N 23/046; G01T 1/1606; H05G 1/08
See application file for complete search history.

(56) References Cited

FOREIGN PATENT DOCUMENTS

| | | |
|---|---|---|
| JP | 2011-024773 A | 2/2011 |
| JP | 2011-217805 A | 11/2011 |
| JP | 2012-034901 A | 2/2012 |
| WO | WO 2012/173206 A1 | 12/2012 |

OTHER PUBLICATIONS

International Search Report dated Apr. 1, 2014 in PCT/JP2013/085146 filed Dec. 27, 2013.

* cited by examiner

IMAGING ENERGY RANGE (20 keV TO 80 keV)
CORRECTION ENERGY RANGE (80 keV TO 160 keV)

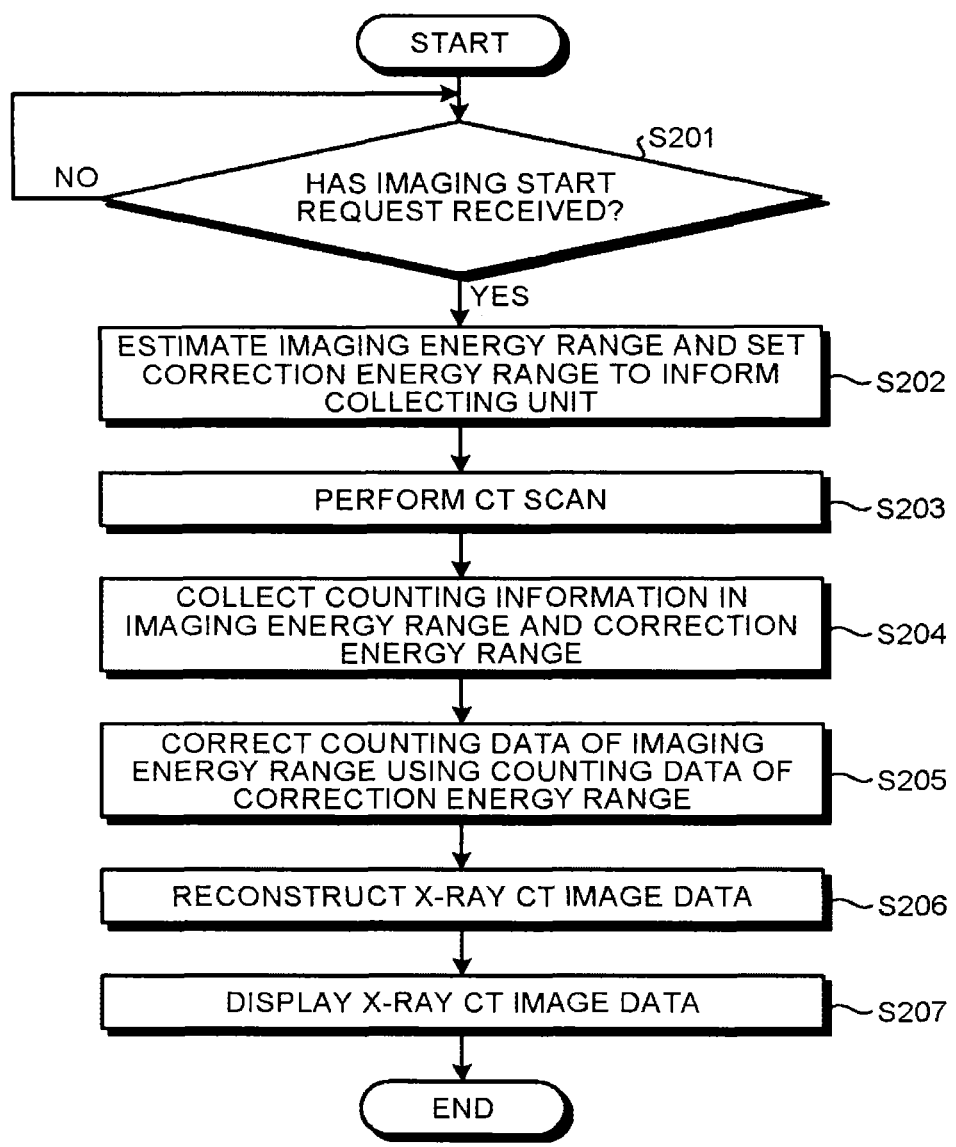

X-RAY COMPUTED TOMOGRAPHY APPARATUS AND CONTROL METHOD

CROSS-REFERENCE TO RELATED APPLICATIONS

This application is a continuation of PCT international application Ser. No. PCT/JP2013/085146 filed on Dec. 27, 2013 which designates the United States, incorporated herein by reference, and which claims the benefit of priority from Japanese Patent Application No. 2012-288495, filed on Dec. 28, 2012, the entire contents of which are incorporated herein by reference.

FIELD

Embodiments described herein relate generally to an X-ray computed tomography (CT) apparatus and a control method.

BACKGROUND

Recently, X-ray CT apparatuses that perform photon counting CT using a photon-counting mode detector are being developed. Unlike an integral mode detector used in a conventional X-ray CT apparatus, the photon-counting mode detector outputs a signal from which X-ray photons that have passed through a subject can be individually counted. Therefore, in the photon counting CT, an X-ray CT image having a high signal-to-noise (S/N) ratio can be reconstructed.

Moreover, the signal output by the photon-counting mode detector can be used for measurement (discrimination) of the energy of an X-ray photon. Therefore, in photon counting CT, data that is collected by irradiating X-rays with one tube voltage can be separated into energy components to be made into images. For example, in photon counting CT, an image that enables identification of a material using a difference in the K absorption edge can be generated.

However, in photon counting CT, noise components such as scattered radiation is also counted, and therefore, the quality of reconstructed images can be deteriorated.

BRIEF DESCRIPTION OF THE DRAWINGS

FIG. 14 is a flowchart for explaining an example of a processing performed by an X-ray CT apparatus according to the third embodiment.

DETAILED DESCRIPTION

An X-ray computed tomography (CT) apparatus includes a detector, and processing circuitry. The detector is configured to output, at each incidence of an X-ray photon, a signal enabling measurement of an energy value of the X-ray photon. Processing circuitry is configured to estimate an energy range to be used for imaging based on an imaging condition and to reconstruct X-ray CT image data using counting information to which an energy value within the energy range is associated among pieces of counting information that are collected from individual signals output by the detector at each incidence of an X-ray photon that has been irradiated from an X-ray tube and has passed through a subject, and in which a counting value and an energy value of X-ray photons incident to the detector are associated with each other.

An X-ray computed tomography (CT) apparatus includes a detector, a control unit, and an image reconstructing unit. The detector outputs, at each incidence of an X-ray photon, a signal enabling measurement of an energy value of the X-ray photon. The control unit estimates an energy range to be used for imaging based on an imaging condition. The image reconstructing unit reconstructs X-ray CT image data using counting information to which an energy value within the energy range is associated among pieces of counting information that are collected from individual signals output by the detector at each incidence of an X-ray photon that has been irradiated from an X-ray tube and has passed through a subject, and in which a counting value and an energy value of X-ray photons incident to the detector are associated with each other.

Embodiments of an X-ray CT apparatus are explained in detail below with reference to the accompanying drawings.

The X-ray CT apparatus explained in the following embodiments is an apparatus that can perform photon counting CT. That is, the X-ray CT apparatus explained in the following embodiments is an apparatus that can reconstruct X-ray CT-image data having a high S/N ratio by counting photons (X-ray photons) derived from X-rays that have passed through a subject using not a conventional integral mode (current mode measurement) detector but a photon-counting mode detector.

Individual photons have different energies. In photon counting CT, by measuring an energy value of a photon, information of energy components of X-rays can be acquired. In photon counting CT, data collected by irradiating X-rays with one tube voltage can be separated into energy components to be made into images.

First Embodiment

Figure 1:
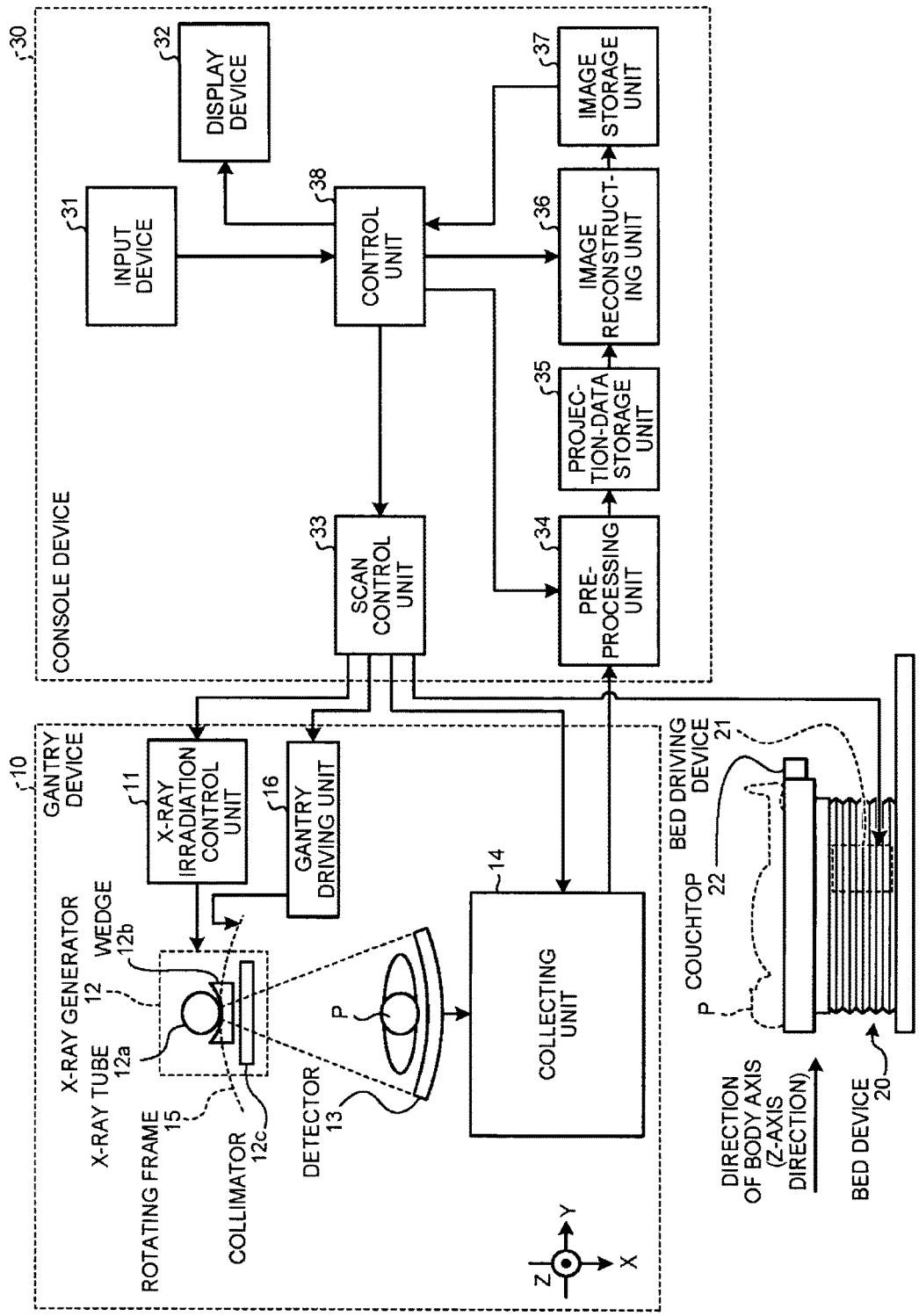
FIG. 1 is a schematic diagram illustrating a configuration example of an X-ray CT apparatus according to a first embodiment.

First, a configuration of an X-ray CT apparatus according to a first embodiment is explained. FIG. 1 is a schematic diagram illustrating a configuration example of the X-ray CT apparatus according to the first embodiment. As shown in FIG. 1, the X-ray CT apparatus according to the first embodiment includes a gantry device 10, a bed device 20, and a console device 30.

The gantry device 10 is a device that irradiates X-rays to a subject P and counts X-rays that have passed through the subject P, and includes an X-ray irradiation control unit 11, an X-ray generator 12, a detector 13, a collecting unit 14, a rotating frame 15, and a gantry driving unit 16.

The rotating frame 15 supports the X-ray generator 12 and the detector 13 across the subject P in between so as to oppose to each other, and is an annular frame that rotates in high speed along a circular orbit having the subject P in a center, being driven by the gantry driving unit 16 described later.

The X-ray generator 12 is a device that generates X-rays and irradiates the generated X-rays to the subject P, and includes an X-ray tube 12a, a wedge 12b, and a collimator 12c.

The X-ray tube 12a is a vacuum tube that irradiates X-ray beams to the subject P with a high voltage provided by the X-ray generator 12 described later, and irradiates X-ray beams to the subject P along with rotation of the rotating frame 15. The X-ray tube 12a generates X-ray beams that radiates in a fan angle and a corn angle.

The wedge 12b is an X-ray filter to adjust the dose of X-rays irradiated from the X-ray tube 12a. Specifically, the wedge 12b is a filter to attenuate X-rays irradiated from the X-ray tube 12a by letting the X-rays pass through such that the X-rays to be irradiated to the subject P from the X-ray tube 12a have a predetermined distribution.

For example, the wedge 12b is a filter that is obtained by processing aluminum to have a predetermined target angle and a predetermined thickness. Wedges are also called wedge filters or bow-tie filters. Moreover, the X-ray CT apparatus according to the present embodiment has various kinds of the wedges 12b to be switched according to an imaging condition. For example, the X-ray-irradiation control unit 11 described later switches the wedges 12b according to an imaging condition. For example, the X-ray generator 12 has two kinds of wedges.

The collimator 12c is a slit to narrow an irradiation range of X-rays the dose of which is adjusted by the wedge 12b by the control by the X-ray-irradiation control unit 11 described later.

The X-ray-irradiation control unit 11 is a device to provide a high voltage to the X-ray tube 12a as a high-voltage generating unit, and the X-ray tube 12a generates X-rays with the high voltage provided by the X-ray-irradiation control unit 11. The X-ray-irradiation control unit 11 adjusts the dose of X-rays to be irradiated to the subject P by adjusting a tube voltage and a tube current that are provided to the X-ray tube 12a.

Furthermore, the X-ray-irradiation control unit 11 performs switching of the wedges 12b. Moreover, the X-ray-irradiation control unit 11 adjusts an X-ray irradiation range (the fan angel or the corn angle) by adjusting a degree of opening of the collimator 12c. In the present embodiment, various kinds of wedges may be manually switched by an operator.

The gantry driving unit 16 rotates the X-ray generator 12 and the detector 13 along a circular orbit having the subject P in a center by driving the rotating frame 15 to rotate.

The detector 13 outputs, at each incidence of an X-ray photon, a signal from which an energy value of the X-ray photon can be measured. The X-ray photon is, for example, an X-ray photon that has been irradiated from the X-ray tube 12a and has passed through the subject P. The detector 13 has detector elements that output a one-pulse electric signal (analog signal) at each incidence of an X-ray photon. By counting the number of the electric signals (pulses), the number of X-ray photons incident to each of the detector elements can be counted. Moreover, by performing an arithmetic processing to the signal, the energy value of the X-ray photon that caused the output of the signal can be measured. A method of measuring the energy value is explained in detail later.

The detector element described above is, for example, a semiconductor element of cadmium telluride (CdTe). In this case, the detector 13 shown in FIG. 1 is to be a direct conversion detector that directly converts an incident X-ray photon into an electric signal. The present embodiment is also applicable to a case in which a detector element 131 is formed with, for example, a semiconductor of cadmium zinc telluride (CdZnTe). Furthermore, the detector element described above may be formed with, for example, a scintillator and an optical sensor such as a photomultiplier tube. In this case, the detector 13 shown in FIG. 1 is a indirect conversion detector that converts an incident X-ray photon into a scintillator light by the scintillator, and converts the scintillator light into an electric signal by the optical sensor such as the photomultiplier tube.

Figure 2:
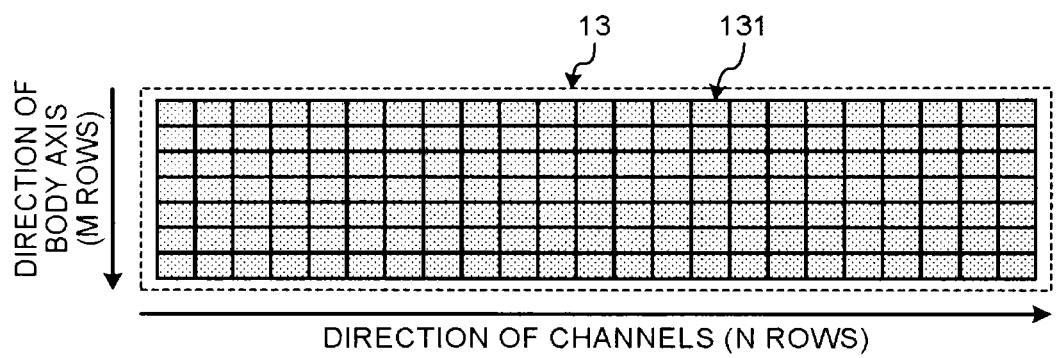
FIG. 2 is a schematic diagram for explaining an example of a detector according to the first embodiment.

FIG. 2 is a schematic diagram for explaining an example of the detector according to the first embodiment. For example, the detector 13 shown in FIG. 1 is an area detector in which the detector elements 131 that are formed with cadmium telluride are arranged N rows in a direction of channels (Y-axis direction in FIG. 1), and M rows in a direction of a body axis (Z-axis direction in FIG. 1). The detector element 131 outputs a one-pulse electric signal upon incidence of a photon. By discriminating individual pulses that are output by the detector element 131, the number of X-ray photons incident to the detector element 131 can be counted. Furthermore, by performing an arithmetic processing based on the pulse intensity, the energy value of the counted X-ray photons can be measured.

Although not illustrated, subsequent to the detector 13, an amplifier is arranged for each of the detector elements 131. The amplifier amplifies an electric signal output from the preceding detector element 131, to output to the collecting unit 14 shown in FIG. 1.

Returning to the FIG. 1, the collecting unit 14 collects counting information that is a result of the counting processing using the output signal of the detector 13. That is, the collecting unit 14 discriminates each of the signals that are output from the detector 13 to collect the counting information. The counting information is information that is collected from each of the signals that are output by the detector 13 (the detector elements 131) at each incidence of an X-ray photon that has irradiated from the X-ray tube 12a and passed through the subject P. Specifically, it is information in which the counting value and the energy value of X-ray photons incident to the detector 13 (the detector elements 131) are associated with each other. The collecting unit 14 transmits the collected counting information to the console device 30.

Figure 3A:
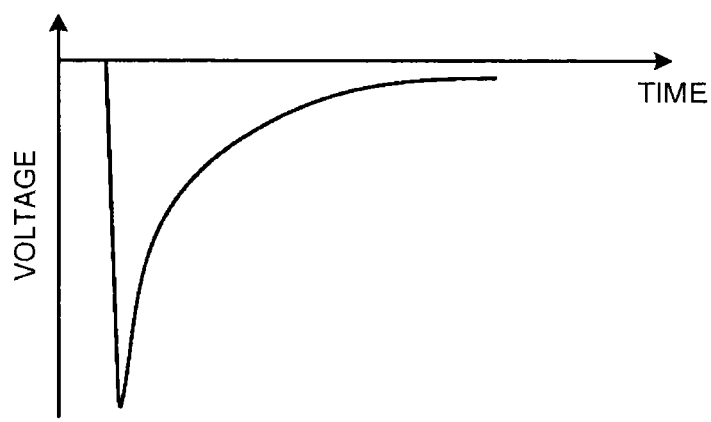
FIG. 3A and FIG. 3B are diagrams for explaining an example of an energy measurement processing performed by a collecting unit shown in FIG. 1.
Figure 3B:
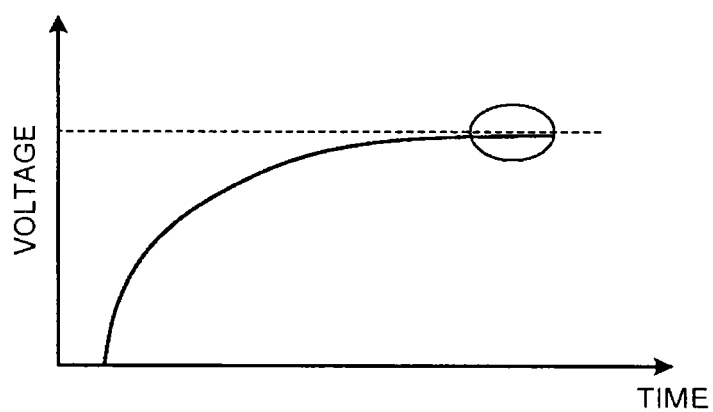

Specifically, the collecting unit 14 collects positions of incidence (positions of detection) of X-ray photons counted by discriminating respective pulses output by the detector elements 131, and energy values of the X-ray photons as the counting information for each phase (X-ray tube phase) of the X-ray tube 12a. The collecting unit 14 determines, for example, that the position of the detector element 131 that has output the pulse (electric signal) used for counting as the position of incidence. Moreover, the collecting unit 14 performs a predetermined arithmetic processing on the electric signal to measure the energy value of the X-ray photon. FIG. 3A and FIG. 3B are diagrams for explaining an example of an energy measurement processing performed by the collecting unit shown in FIG. 1.

FIG. 3A shows one example of an electric signal that is output from the detector element 131. For example, an electric signal output from the detector element 131 is output as an electron that is generated with incidence of an X-ray photon transports toward a collector electrode of a positive potential. In this case, the electric signal is an analog signal a negative voltage value of which varies along a time axis as shown in FIG. 3A. As shown in FIG. 3A, the electric signal abruptly rises toward the negative direction soon after the incidence of the X-ray photon, and thereafter, falls toward the positive direction. The electric signal shown in FIG. 3A is a signal that is output by collecting electrons generated with incidence of X-ray photons, and is only one example thereof. The electric signal output at incidence of an X-ray photon may be output as a positive hole that is generated with incidence of an X-ray photon transports toward a collector electrode of a negative potential. In this case, the electric signal output at incidence of an X-ray photon abruptly rises toward the positive direction soon after the incidence of the X-ray photon, and thereafter, falls toward the negative direction. The present embodiment is applicable to both a case in which such a signal is used that electrons generated at incidence of X-ray photons are collected, and a case in which such a signal is used that positive holes generated at incidence of X-ray photons are collected, as the electric signal output at incidence of an X-ray photon. Furthermore, the present embodiment is applicable to a case in which such a signal that electrons generated at incidence of X-rays are collected and such a signal that positive holes generated at incidence of X-rays are collected are used at the same time.

The collecting unit 14 generates a signal (integral signal) that the electric signal shown in FIG. 3A is integrated along a direction of time for a predetermined set time. FIG. 3B indicates an integral signal of the electric signal shown in FIG. 3A. The collecting unit 14 determines a voltage value (hereinafter, convergence value) with which the integral signal reaches a plateau. The collecting unit 14 then calculates an energy value from the convergence value and a system-specific response function. This response function is a function calculated in advance from physical characteristics of the detector elements 131, and is a function to acquire an energy value from the convergence value. For example, the collecting unit 14 holds a table in which the convergence value and the energy value that is acquired by substituting the convergence value into the response function are associated with each other.

The counting information is, for example, information indicating such that 'in X-ray tube phase "α1" at the detector element 131 of position of incidence "P11", the counting value of photons having energy "E1" is "N1" and the counting value of photons having energy "E2" is "N2"'. Alternatively, the counting information is, for example, information indicating such that 'in X-ray tube phase "α1" at the detector element 131 of position of incidence "P11", the counting value of photons having energy "E1" per unit time is "n1" and the counting value of photons having energy "E2" per unit time is "n2"'.

Energy "E1" in the above counting information may be, for example, an energy differential range "E1 to E2". In this case, the counting information is, for example, information indicating such that 'in X-ray tube phase "α1" at the detector element 131 of position of incidence "P11", the counting value of photons having energy differential range "E1 to E2" is "NN1"'. Alternatively, the counting information is, for example, information indicating such that 'in X-ray tube phase "α1" at the detector element 131 of position of incidence "P11", the counting value of photons having energy differential range "E1 to E2" per unit time is "nn1"'. The energy differential range described above is a range for the collecting unit 14 to discriminate the energy value into predetermined granularities to be distributed. Thresholds to set the energy differential range is specified, for example, by a control unit 38 described later.

The collecting unit 14 can be configured in various forms as explained below. In the following, two configuration examples (a first configuration example and a second configuration example) of the collecting unit 14 are explained. The collecting unit 14 configured in the first configuration example includes an analog-to-digital converter (ADC) that is arranged for each of the detector elements 131. For example, the ADC samples analog electric signals to generate integral signals, and outputs a digital signal for which sampling is performed in a region in which the voltage value converges (refer to an elliptic circle shown in FIG. 3B) from the integral signals. The ADC may be arranged, for example, for each channel in which four units of the detector elements 131 are bound.

The digital signal output from the ADC is output to multiple comparators. A threshold is set for each of the comparators. The comparators perform a comparison processing using a response function, and thereby collect counting information of each of the energy differential ranges. The number of energy differential ranges is determined based on the number of comparators that can be arranged in the collecting unit 14. It is also applicable that the ADC calculates the energy value using the response function and the comparator performs the comparison processing.

In the first configuration example described above, the collecting unit 14 collects the counting information in which the counting values of the respective detector elements 131 at the respective X-ray tube phases are distributed to the energy differential ranges. On the other hand, when the counting information in which the counting values of the respective detector elements 131 at the respective X-ray tube phases are distributed to respective energy values is collected, the collecting unit 14 is configured, for example, as in the second configuration example explained below. For example, in the collecting unit 14, an ADC that is capable of high speed sampling (hereinafter, high-speed ADC) is arranged for each of the detector elements 131. The high-speed ADC converts the entire electric signal shown in FIG. 3A and the entire integral signal shown in FIG. 3B into digital signals. In a subsequent stage of each of the high-speed ADCs, for example, a field-programmable gate array (FPGA) is arranged. Each of the FPGAs calculates an energy value from the digital signal output from the high-speed ADC in the preceding stage. When the high-speed ADC described above is used, the collecting processing of the counting information may be performed by the console device 30. In this case, the collecting unit 14 collects digital signals by the high-speed ADC, and transmits the digital signals to a second collecting unit arranged in the console device 30. The second collecting unit collects counting information from the digital signals received from the collecting unit 14.

Returning to FIG. 1, the bed device 20 is an equipment to lay the subject P, and includes a couchtop 22 and a bed driving unit 21 as shown in FIG. 1. The couchtop 22 is a plate on which the subject P is laid, and the bed driving unit 21 moves the subject P into the rotating frame 15 by moving the couchtop 22 in the Z-axis direction.

The gantry device 10 executes, for example, helical scan in which the subject P is helically scanned by rotating the rotating frame 15 while moving the couchtop 22. Alternatively, the gantry device 10 executes conventional scan in which after moving the couchtop 22, the subject P is scanned in a circular orbit by rotating the rotating frame 15 while the position of the subject P is fixed. Alternatively, the gantry device 10 implements the step-and-shoot method in which the conventional scan is performed at multiple scan areas while moving the couchtop 22 at regular intervals.

The console device 30 is a device that accepts an operation of the X-ray CT apparatus by an operator, and reconstructs X-ray CT image data using the counting information that has been collected by the gantry device 10. The console device 30 includes, as shown in FIG. 1, an input device 31, a display device 32, a scan control unit 33, a preprocessing unit 34, a projection-data storage unit 35, an image reconstructing unit 36, an image storage unit 37, and the control unit 38.

The input device 31 has a mouse, a keyboard, and the like for an operator to input various kinds of instructions, and transfers information of the instructions and settings received from the operator to the control unit 38. For example, the input device 31 accepts an imaging condition for X-ray CT image data, a reconstruction condition when the X-ray CT image data is reconstructed, an image processing condition for the X-ray CT image data, and the like.

The display device 32 is a monitor to be referred to by an operator, and displays the X-ray CT image data to the operator based on the control by the control unit 38, and displays a graphical user interface (GUI) to accept various kinds of instructions and settings or the like from the operator through the input device 31.

The scan control unit 33 controls operation of the X-ray-irradiation control unit 11, the gantry driving unit 16, the collecting unit 14, and the bed driving unit 21 based on the control by the control unit 38 described later, and thereby controls the collecting processing of the counting information in the gantry device 10.

The preprocessing unit 34 generates projection data by performing a logarithm conversion processing and a correction processing, such as an offset correction, a responsivity correction, and a beam hardening correction, on the counting information transmitted from the collecting unit 14.

The projection-data storage unit 35 stores projection data that is generated by the preprocessing unit 34. That is, the projection-data storage unit 35 stores the projection data (the corrected counting information) to reconstruct the X-ray CT image data. In the following, the projection data is sometimes described as counting information.

The image reconstructing unit 36 reconstructs X-ray CT image data using the projection data stored in the projection-data storage unit 35. As a reconstruction method, various methods are available, and for example, there is a back projection processing. Furthermore, as the back projection processing, for example, there is a back projection processing by filtered back projection (FBP). Moreover, the image reconstructing unit 36 generates image data by performing various kinds of image processing on the X-ray CT image data. The image reconstructing unit 36 stores X-ray CT image data reconstructed by the image reconstructing unit 36, image data generated by various kinds of image processing in the image storage unit 37, and the like.

In the projection data that is generated from the counting information acquired by the photon counting CT, energy information of X-rays that are attenuated by passing through the subject P is included. Therefore, the image reconstructing unit 36 can reconstruct, for example, X-ray CT image data of a specific energy component. Moreover, the image reconstructing unit 36 can reconstruct, for example, X-ray CT image data of respective energy components.

Furthermore, the image reconstructing unit 36 can generate multiple pieces of X-ray CT image data colored according to energy components by assigning a color according to an energy component of each pixel in the X-ray CT image data of each energy component, and can further generate image data in which these pieces of X-ray CT image data are superimposed.

The image reconstructing unit 36 can generate, by using a material-specific K absorption edge, image data that enables identification of the material. Because the attenuation coefficients of X-rays differ significantly before and after the K absorption edge, the counting values also vary significantly. For example, the image reconstructing unit 36 generates difference image data obtained by performing subtraction between image data that is reconstructed from counting information in a region of energy smaller than a K absorption edge and image data that is reconstructed from counting information in a region of energy larger than the K absorption edge. For example, difference image data that is generated by using a K absorption edge of a principal component of a contrast agent is to be an image in which an area in which the contrast agent is present is mainly imaged. Moreover, other image data that is generated by the image reconstructing unit 36 includes monochromatic X-ray image data, density image data, effective atomic-number image data, and the like.

The control unit 38 controls the entire X-ray CT apparatus by controlling operation of the gantry device 10, the bed device 20, and the console device 30. Specifically, the control unit 38 controls CT scan performed in the gantry device 10 by controlling the scan control unit 33. Moreover, the control unit 38 controls the image reconstruction processing and the image generation processing performed in the console device 30 by controlling the preprocessing unit 34 and the image reconstructing unit 36. Furthermore, the control unit 38 controls to display various kinds of image data stored in the image storage unit 37 on the display device 32.

As above, the entire configuration of the X-ray CT apparatus according to the first embodiment has been explained. According to the configuration, the X-ray CT apparatus according to the first embodiment performs reconstruction of X-ray image data having higher quality compared to a case of conventional integral mode CT, by measuring energy of individual X-ray photons incident to the detector 13 by the photon counting CT. However, in the photon counting CT, noise components such as scattered radiation are also counted, and therefore, improvement of the image quality of X-ray image data cannot sometimes be achieved.

Accordingly, to improve the image quality of images obtained by the photon counting CT, control by the control unit 38 explained below is performed in the X-ray CT apparatus according to the first embodiment.

That is, the control unit 38 according to the first embodiment estimates an energy range of an X-ray photon incident to the detector 13. The energy range is a range from which an energy range that is assumed that the X-ray photon incident to the detector 13 does not hold is excluded. The range to be excluded is a range that is estimated as an energy range of noise components, and the energy range that the control unit 38 estimates is an imaging energy range that is used for imaging.

Subsequently, the image reconstructing unit 36 reconstructs X-ray CT image data using counting information to which an energy value within the energy range is associated among the counting information, by the control of the control unit 38. In the first embodiment, the control unit 38 sends an instruction to collect counting information of an energy value within the energy range to the collecting unit 14. As a result, projection data that is generated from only the counting information of energy values within the energy range is stored in the projection-data storage unit 35, and the image reconstructing unit 36 reconstructs X-ray CT image data using such projection data.

Figure 4:
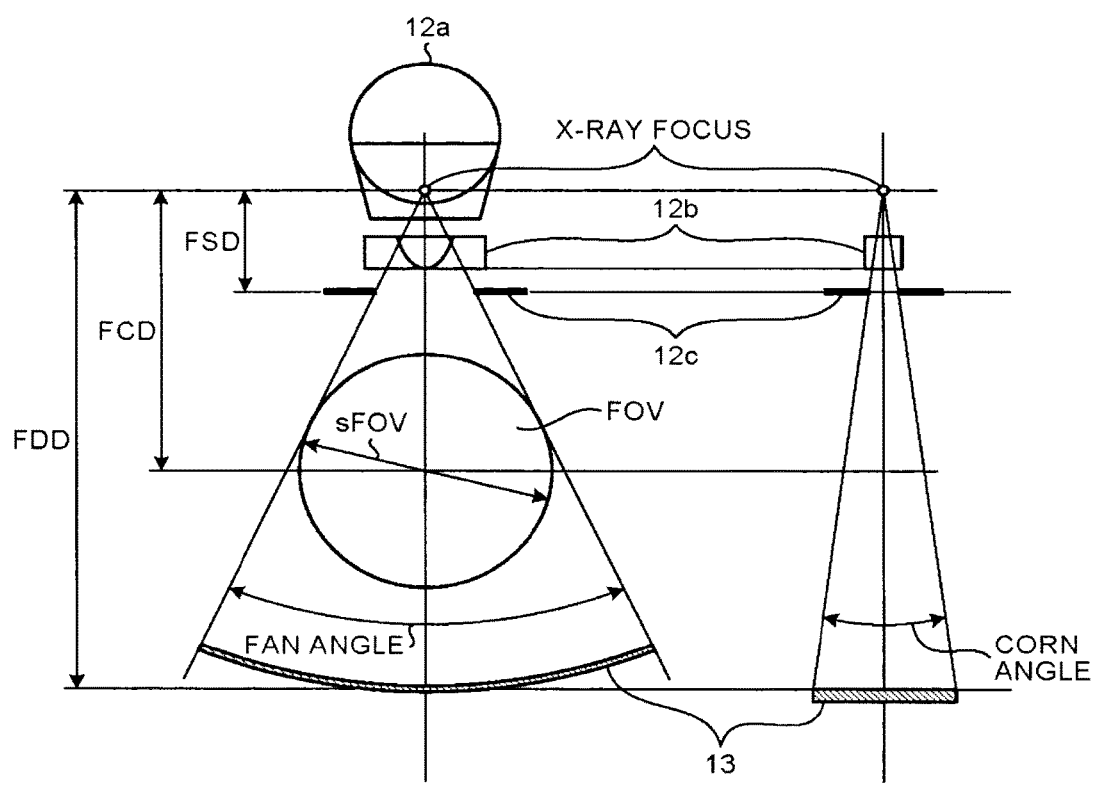
FIG. 4, FIG. 5 and FIG. 6 are diagrams for explaining a processing performed by a control unit according to the first embodiment.
Figure 5:
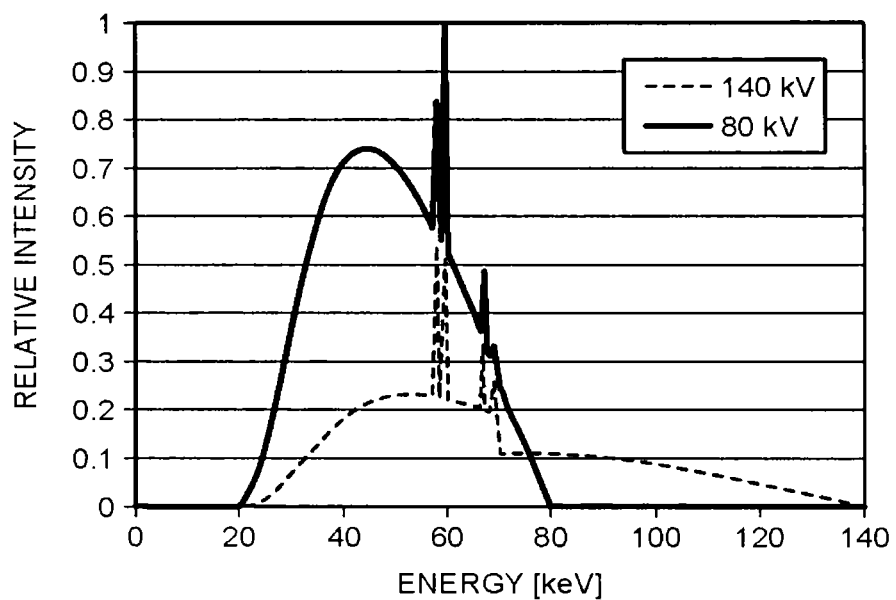
Figure 6:
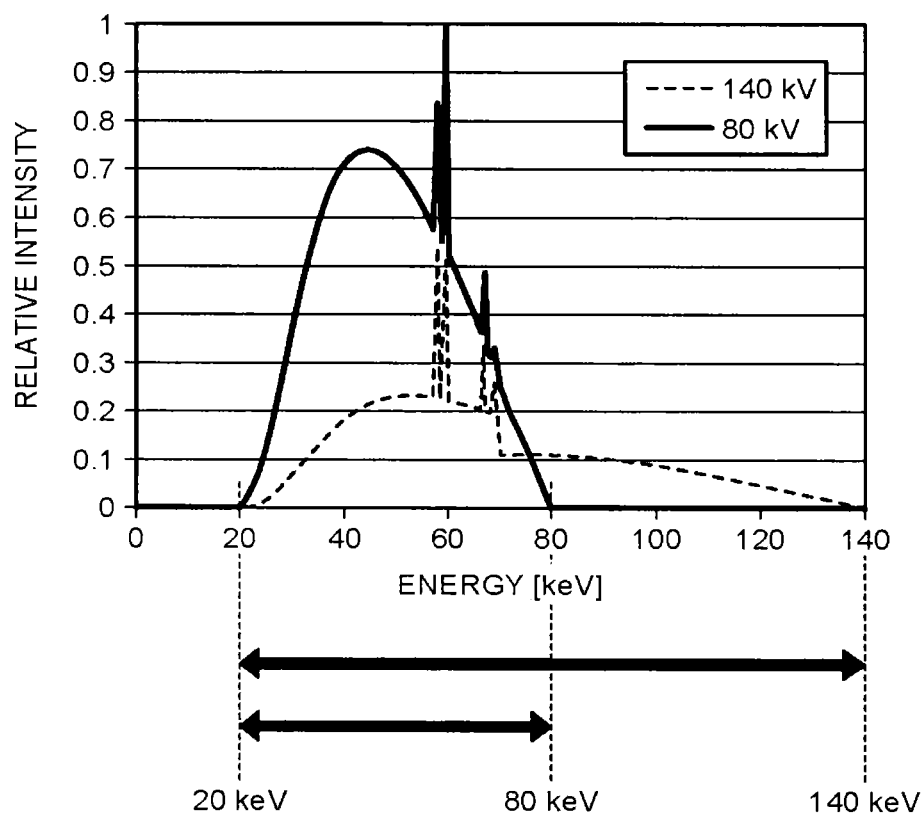

The control unit 38 according to the first embodiment estimates the energy range based on an imaging condition of X-ray image data, namely, an X-ray irradiation condition included in an imaging condition. That is, the control unit 38 according to the first embodiment estimates the energy range to be used for imaging based on the imaging condition. In the following, the processing performed by the control unit 38 according to the first embodiment is explained using FIG. 4, FIG. 5, and FIG. 6. FIG. 4, FIG. 5, and FIG. 6 are diagrams for explaining the processing performed by the control unit according to the first embodiment.

At irradiation of X-rays, the X-ray tube 12a irradiates X-rays through the wedge 12b as shown in FIG. 4. By the wedge 12b, the dose of the X-rays irradiated from the X-ray tube 12a is adjusted. Furthermore, the irradiation range of the X-rays is adjusted by the wedge 12b and the opening of the collimator 12c. Thus, an X-ray beam having scattering angles of the fan angle and the corn angle from an X-ray focus is irradiated from the X-ray tube 12a as shown in FIG. 4. FOV shown in FIG. 4 indicates a field of view at the time of imaging. The diameter of the FOV (refer to sFOV in the diagram) is determined by the distance between the X-ray focus and the detector 13 (inner diameter of the rotating frame 15), the irradiation range of X-rays, and the like. The FOV is also called an imaging field of view or an effective field of view.

Furthermore, FSD shown in FIG. 4 represents a distance between the X-ray focus and the collimator 12c being a slit, and is called focus slit distance. Moreover, the FCD shown in FIG. 4 represents a distance between the X-ray focus and a center of the FOV, and is called focus center distance. Furthermore, FDD shown in FIG. 4 represents a distance between the X-ray focus and the detector 13, and is called focus detector distance.

The wedges 12b are switched according to an X-ray irradiation condition. Moreover, a tube voltage to be provided to the X-ray tube 12a is set as the X-ray irradiation condition. FIG. 5 shows a distribution (energy spectrum) of energy values (unit: keV) of X-ray photons that is observed when X-rays are irradiated from the X-ray tube 12a using the wedge 12b formed with aluminum of "thickness: 5 millimeters (mm), target angle: 7 degrees". The horizontal axis in FIG. 5 indicates energy (unit: keV), and the vertical axis in FIG. 5 indicates relative intensity of X-rays. In the example shown in FIG. 5, for easier comparison of two energy spectrums observed with different tube voltages, an actuary measured X-ray intensity is normalized setting the maximum value of actuary measured X-ray intensity as "1".

An energy spectrum A indicated by a solid line in FIG. 5 is an energy spectrum that is observed when the tube voltage is 80 kV. Moreover, an energy spectrum B indicated by a dotted line in FIG. 5 is an energy spectrum that is observed when the tube voltage is 140 kV.

X-rays generated by the X-ray tube 12a are attenuated by passing through the wedge 12b as described above. Therefore, X-rays in a range in which X-rays have been completely attenuated by the wedge 12b are not supposed to be irradiated to the subject P. In other words, X-ray photons that have passed through the subject P should not include X-ray photons having energy values in the energy range completely attenuated by the wedge 12b. Counting information of an energy value in the energy range completely attenuated by the wedge 12b is regarded as counting information of noise components such as scattered radiation. The counting information of noise components causes reduction in image quality.

For example, referring to the energy spectrum A and the energy spectrum B shown in FIG. 5, the energy value of the X-ray photon takes a value larger than 20 keV. This indicates that among X-rays generated by the X-ray tube 12a, X-rays in an energy range of approximately 20 keV or smaller are completely attenuated by the wedge 12b formed with aluminum of "thickness: 5 mm, target angle: 7 degrees".

The control unit 38 acquires an energy range (attenuation energy range) that is absorbed by the wedge 12b, based on a material and a shape of the wedge 12b to be used in imaging. The control unit 38 then estimates the energy range regarding an upper limit value of the acquired energy range (attenuation energy range) as a lower limit threshold. For example, the control unit 38 holds attenuation energy ranges of the respective wedges 12b used in the X-ray CT apparatus in a form of table, and acquires an attenuation energy range of the wedge 12b to be used in imaging. Alternatively, the control unit 38 calculates an attenuation energy range, for example, from information about a material and a shape of the wedge 12b to be used in the X-ray CT apparatus.

For example, the control unit 38 understands that the attenuation energy range of the wedge 12b is 20 keV or smaller from the material and the shape, and therefore, sets the lower limit threshold of the energy value to "20 keV" as shown in FIG. 6.

Furthermore, the control unit 38 estimates the energy range using a tube voltage at the time of imaging. The X-ray tube 12a cannot radiate an X-ray having an energy value larger than a supplied tube voltage. For example, in the energy spectrum A when the tube voltage is 80 kV, the maximum value of the energy value of X-ray photons is 80 keV as shown in FIG. 5. Moreover, in the energy spectrum B when the tube voltage is 140 kV, the maximum value of the energy value of X-ray photons is 140 keV. Therefore, an energy range in which a value larger than a value of the tube voltage set at the time of imaging is measured is also regarded as noise components. The counting information of noise components causes reduction in image quality.

Therefore, the control unit 38 acquires an upper limit energy value of X-ray photons irradiated from the X-ray tube 12a based on a tube voltage supplied to the X-ray tube 12a at the time of imaging of the subject P. The control unit 38 then estimates the energy range, regarding the acquired upper limit energy value as the upper limit threshold.

For example, the control unit 38 regards the upper limit threshold of the energy range as "80 keV" when the tube voltage at the time of imaging is 80 kV as shown in FIG. 6. Moreover, for example, the control unit 38 regards the upper limit threshold of the energy range as "140 keV" when the tube voltage at the time of imaging is 140 kV as shown in FIG. 6.

As described, the control unit 38 sets the energy range by regarding an upper limit value of an attenuation energy range acquired based on a material and a shape of the wedge 12b to be used for imaging as the lower limit threshold, and a maximum energy value according to a tube voltage set at the time of imaging as the upper limit threshold. For example, when imaging at a "tube voltage: 80 kV" is performed with the wedge 12b formed with aluminum of "thickness: 5 mm, target angle: 7 degrees", the control unit 38 estimates "20 keV to 80 keV" as the energy range as shown in FIG. 6. Furthermore, for example, imaging at a "tube voltage: 140 kV" is performed with aluminum of "thickness: 5 mm, target angle: 7 degrees", the control unit 38 estimates "20 keV to 140 keV" as the energy range as shown in FIG. 6.

The energy range estimated by the control unit 38 is to be an imaging energy range to set counting information to be used for imaging. The control unit 38 informs, for example, "20 keV to 140 keV" to the collecting unit 14. The collecting unit 14, for example, sets "20 keV" and "140 keV" as the thresholds in the comparator and the FPGA. The control unit 38 then controls the scan control unit 33 to perform CT scan. The CT scan is, for example, conventional scan or helical scan.

The collecting unit 14 discards a counting value of an energy value (E) corresponding to "E<20 keV" and "E>140 keV", and sends counting information of an energy value corresponding to "20 keV<E<140 keV" to the console device 30. Thus, the image reconstructing unit 36 reconstructs X-ray CT image data using the counting information of the imaging energy range.

Figure 7:
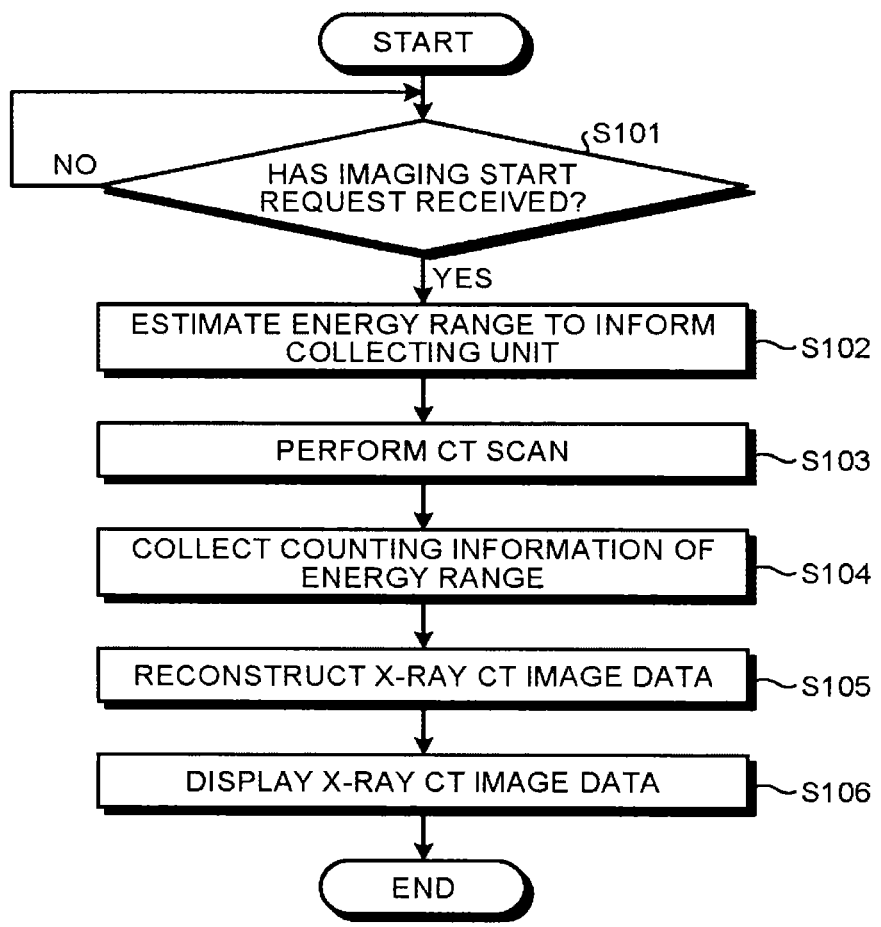
FIG. 7 is a flowchart for explaining an example of a processing performed by an X-ray CT apparatus according to the first embodiment.

Next, the processing of the X-ray CT apparatus according to the first embodiment is explained using FIG. 7. FIG. 7 is a flowchart for explaining an example of the processing performed by the X-ray CT apparatus according to the first embodiment.

As shown in FIG. 7, the control unit 38 of the X-ray CT apparatus according to the first embodiment judges whether an imaging start request has been received from an operator (step S101). When an imaging start request has not been received (step S101: NO), the control unit 38 waits until an imaging start request is received.

On the other hand, when an imaging start request has been received (step S101: YES), the control unit 38 estimates the energy range (imaging energy range) based on an X-ray irradiation condition received together with the imaging start request, to inform the collecting unit 14 (step S102). The control unit 38 then controls to perform CT scan (step S103).

The collecting unit 14 collects counting information of the energy range (step S104), and the image reconstructing unit 36 reconstructs X-ray CT image data (step S105). Specifically, the image reconstructing unit 36 reconstructs X-ray CT image data using projection data that is generated from the counting information of the energy range.

The display device 32 then displays the X-ray CT image data based on the control of the control unit 38 (step S106), and the processing is ended.

As described above, in the first embodiment, the control unit 38 acquires an energy range of noise components based on an X-ray irradiation condition at the time of imaging of the subject P, and estimates an energy range that is obtained by excluding the energy range of noise components, as the energy range (imaging energy range) to be used for imaging. Thus, the image reconstructing unit 36 performs the reconstruction processing using the counting information from which the noise components are removed. Therefore in the first embodiment, it is possible to improve the quality of images acquired by the photon counting CT.

In the present embodiment, a case in which the control unit 38 controls the collecting unit 14 to collect counting information of the energy range to perform the reconstruction processing using the counting information of the energy range has been explained. However, in the present embodiment, the control for performing the reconstruction processing using the counting information of the energy range may be performed on the image reconstructing unit 36.

In this case, the control unit 38 sends an instruction that the reconstruction processing is performed using counting information of an energy value within the energy range among pieces of counting information collected by the collecting unit 14 to the image reconstructing unit 36. That is, in the above example, the counting information collected by the collecting unit 14 is selected in the console device 30, and thus, the reconstruction processing using counting information of the energy range is performed. If the collecting unit 14 is designed as the second configuration example describe above, the control unit 38 can perform the above control without performing threshold setting to the collecting unit 14. If the collecting unit is designed as the first configuration example describe above, the control unit 38 is required to set the upper limit threshold and the lower limit threshold of the imaging energy range to the collecting unit 14.

Moreover, the first embodiment is applicable to a case in which the energy range is estimated only with the lower limit threshold based on the wedge 12b to be used for imaging, or a case in which the energy range is estimated only with the upper limit threshold based on a tube voltage at the time of imaging.

Second Embodiment

Figure 8:
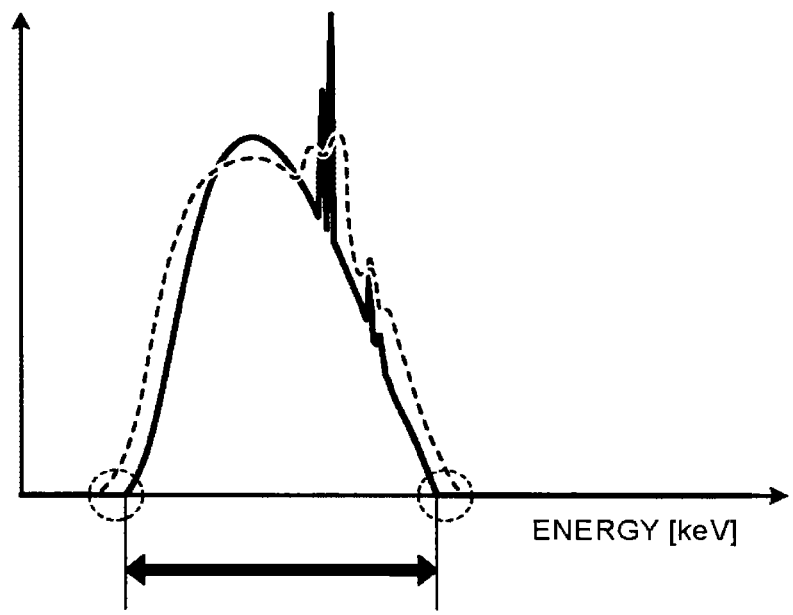
FIG. 8, FIG. 9 and FIG. 10 are diagrams for explaining a second embodiment.
Figure 9:
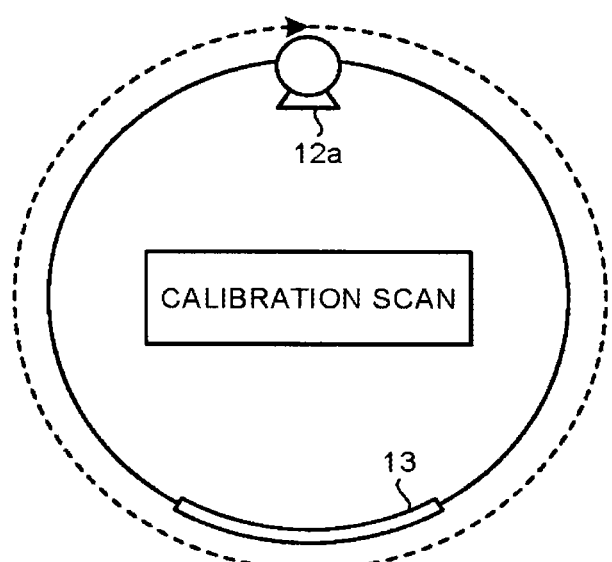
Figure 10:
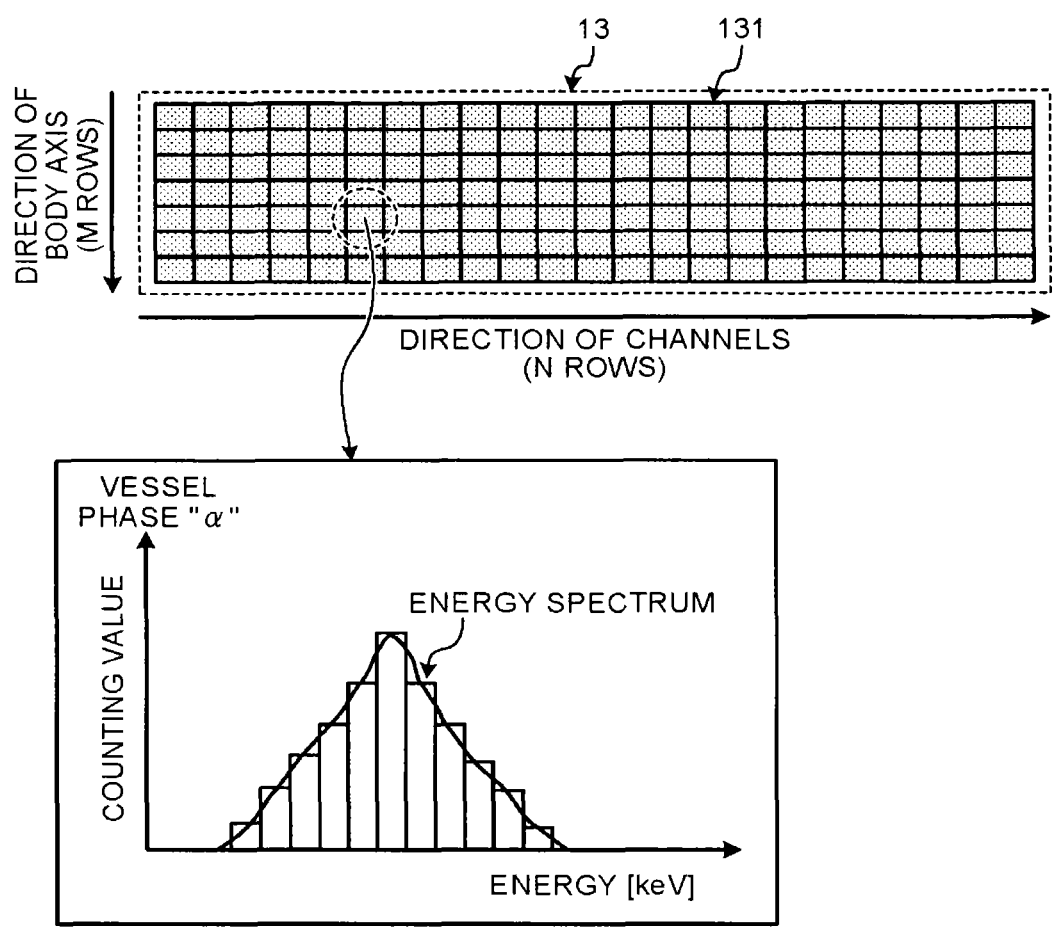

In the first embodiment, a case in which the imaging energy range is estimated using a lower limit threshold and an upper limit threshold that are uniquely determined according to an X-ray irradiation condition has been explained. In the second embodiment, a case in which the imaging energy range is estimated from actuary measured data is explained using FIG. 8, FIG. 9, and FIG. 10. FIG. 8, FIG. 9, and FIG. 10 are diagrams for explaining the second embodiment.

An X-ray CT apparatus according to the second embodiment is configured similarly to the X-ray CT apparatus according to the first embodiment explained using FIG. 1. However, the control unit 38 according to the second embodiment estimates the energy range for imaging by a method different from the method explained in the first embodiment.

The electric signal output from the detector 13 is a result of a phenomenon caused by an X-ray photon that is a particle having dynamic statistical properties, and therefore, has statistical fluctuations. That is, an energy value that is measured by using the electric signal output from the detector 13 has statistical fluctuations. The statistical fluctuations are defined as energy resolution. The energy resolution depend on a type of the detector 13. As explained in the first embodiment, the photon counting mode detector that is used as the detector 13 is mainly divided into a direct detector and an indirect detector.

Generally, the energy resolution of direct detectors is higher than the energy resolution of indirect detectors. For example, the energy resolution can be expressed as a Gaussian curve, and a full width at half maximum of the energy resolution of direct detectors is narrower than a full width at half maximum of the energy resolution of indirect detectors.

An energy spectrum indicated by a solid line in FIG. 8 is an example of an energy spectrum when a direct detector is used as the detector 13. For example, the energy spectrum indicated by the solid line in FIG. 8 is an energy spectrum that is observed when imaging at the "tube voltage: 80 kV" is performed with the wedge 12b formed with aluminum of "thickness: 5 mm, target angle: 7 degrees".

When a direct detector having a high energy resolution is used, the energy range that is estimated by the method explained in the first embodiment almost agrees with a range from a minimum value to a maximum value of energy values observed in the energy spectrum indicated by the solid line in FIG. 8.

On the other hand, an energy spectrum indicated by a dotted line in FIG. 8 is an energy spectrum when an indirect detector is used under the same X-ray irradiation condition as that under which the energy spectrum indicated by the solid line in FIG. 8 is obtained. By using the indirect detector having low energy resolution, in the energy spectrum indicated by the dotted line in FIG. 8, the peak spreads and the peak value is low compared to the energy spectrum indicated by the solid line in FIG. 8, Moreover, because the energy resolution is low, the minimum value of the energy value observed in the energy spectrum indicated by the dotted line in FIG. 8 is smaller than the lower limit threshold of the energy range estimated by the method explained in the first embodiment. Because the energy resolution is low, the maximum value of the energy value observed in the energy spectrum indicated by the dotted line in FIG. 8 is larger than the upper limit threshold of the energy range estimated by the method explained in the first embodiment.

Even with the direct detector, the energy resolution depends on age deterioration of the detector element 131 or types of the detector element 131. Therefore, the phenomenon shown in FIG. 8 can happen even with a direct detector. In this case, if the energy range that is estimated by the method explained in the first embodiment is used, an energy range that can be used for imaging is also discarded as that of noise components.

Therefore, the control unit 38 according to the second embodiment estimates an energy range to be used for imaging based on energy resolution of the detector 13 used for imaging. Specifically, the control unit 38 according to the second embodiment irradiates X-rays from the X-ray tube 12a to the detector 13 in a state in which the subject P is not mounted. The control unit 38 according to the second embodiment then collects energy spectrums at the respective detector elements 131 constituting the detector 13. That is, the control unit 38 according to the second embodiment controls to perform calibration scan in the state in which the subject P is not mounted as shown in FIG. 9. The control unit 38 controls to perform the calibration scan under an X-ray irradiation condition same as that of CT scan for actual imaging. The control unit 38 rotates the X-ray tube 12a and the detector 13 once while irradiating X-rays from the X-ray tube 12a under the X-ray irradiation condition same as that of CT scan for actual imaging as shown in FIG. 9.

FIG. 10 shows an example of an energy spectrum that is collected from one of the detector elements 131 constituting the detector 13 at a tube phase "α". The collecting unit 14 generates a histogram in which counting values are aligned in the order of magnitude of energy values, from the counting information collected using the electric signals that are output from the detector elements 131 at the tube phase "α". The collecting unit 14 transmits the generated histogram to the control unit 38, for example, through the preprocessing unit 34. Alternatively, the collecting unit 14 directly transmits the generated histogram to the control unit 38. The control unit 38 generates an energy spectrum based on the histogram received from the collecting unit 14. The present embodiment is also applicable to a case in which the collecting unit 14 generates an energy spectrum shown in FIG. 10.

The control unit 38 according to the second embodiment sets a lower limit threshold and an upper limit threshold from a minimum value and a maximum value of energy values in all of the collected energy spectrums, to estimate the energy range (imaging energy range). For example, the control unit 38 sets a energy value minimized at the smallest value in each of the collected energy spectrums as the lower limit threshold and an energy value maximized at the largest value in each of the collected energy spectrums as the upper limit threshold. Alternatively, the control unit 38 set a statistical minimum value and a statistical maximum value of energy values in all of the collected energy spectrums as the lower limit threshold and the upper limit threshold, respectively, to estimates the energy range (imaging energy range).

For example, the control unit 38 sets a mean value of smallest values in all of the collected energy spectrums as the lower limit threshold, and a mean value of largest values in all of the collected energy spectrums as the upper limit threshold. Alternatively, for example, the control unit 38 sets a median value of smallest values in all of the collected energy spectrums as the lower limit threshold, and a median value of largest values in all of the collected energy spectrums as the upper limit threshold.

A lower limit threshold set in the second embodiment is to be a value equal to or smaller than the lower limit threshold that is determined by the wedge 12b used for imaging. Moreover, an upper limit threshold set in the second embodiment is to be a value equal to or larger than the upper limit threshold that is determined by the tube voltage at the time of imaging.

The present embodiment is also applicable to a case in which calibration scan is performed with one X-ray tube phase when it is assumed that electric signals output from the detector 13 are identical among respective X-ray tube phases. Alternatively, the present embodiment is applicable to a case in which calibration scan is performed only for some X-ray tube phases. Moreover, the present embodiment is applicable to a case in which calibration scan is performed using one of the detector elements 131 or some of the detector elements 131 selected from all of the detector elements 131.

However, the X-ray intensity within an irradiation area that is determined by the wedge 12b and the collimator 12c is not always stable. Furthermore, output properties of the detector elements 131 can vary according to temperature and the like depending on an X-ray tube phase. Therefore, it is preferable that the calibration scan is performed rotating 360 degrees so that energy spectrums of all X-ray tube phases at which the CT scan for actual imaging is performed are acquired, and that the energy spectrums are collected from the all of the detector elements 131 constituting the detector 13.

Before actual imaging, the calibration scan is performed in agreement with the X-ray irradiation condition for actual imaging. Alternatively, the calibration scan may be performed regularly under each of various kinds of X-ray irradiation conditions that can be set in the X-ray CT apparatus. In this case, the control unit 38 estimates an energy range for each of the X-ray irradiation conditions in advance. Alternatively, in this case, the control unit 38 estimates an energy range before actual imaging, referring to calibration data that meets the X-ray irradiation condition of the actual imaging.

The processing performed by the X-ray CT apparatus according to the second embodiment is the same except that the estimation processing performed at step S102 is performed using the energy spectrums collected by the calibration scan, and therefore, explanation thereof is omitted. Moreover, what has been explained in the first embodiment is applicable similarly to the second embodiment except that the method of estimating an energy range is different. For example, in the second embodiment also, selection to acquire counting information of the energy range may be performed in the gantry device 10 or in the console device 30.

As described above, in the second embodiment, an imaging energy range according to physical characteristics (response function) of the detector 13 used for imaging is estimated based on actual measured data. Therefore, in the second embodiment, the quality of images that are acquired by the photon counting CT can be reliably improved.

Third Embodiment

Figure 11:
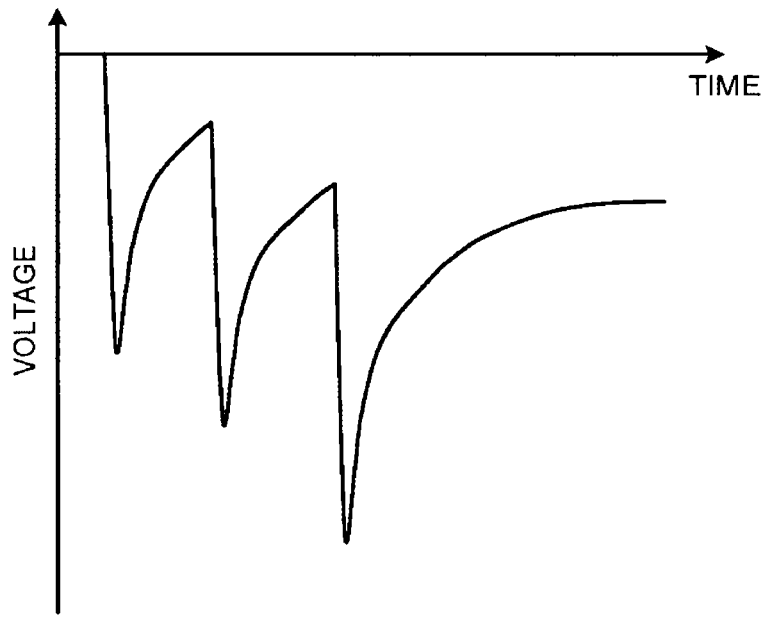
FIG. 11, FIG. 12, FIG. 13A and FIG. 13B are diagrams for explaining a third embodiment.
Figure 12:
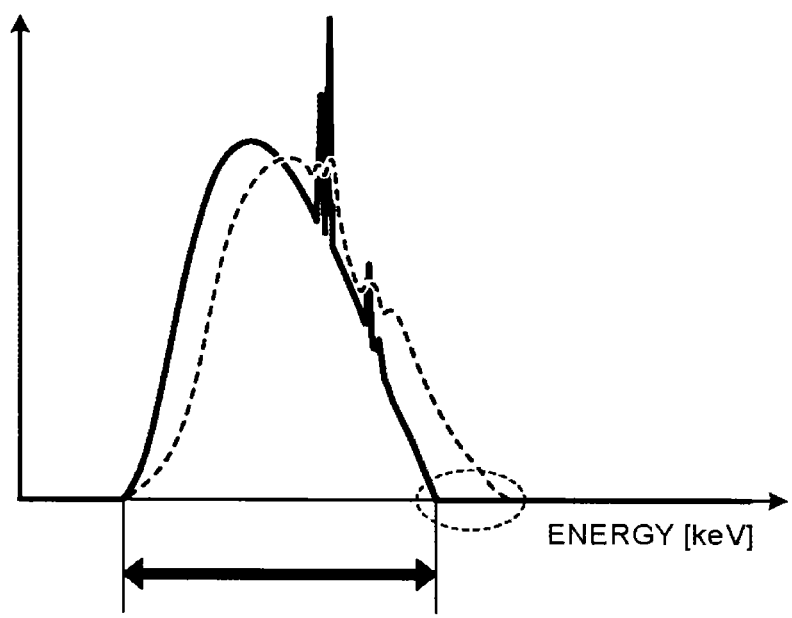
Figures 13A, 13B:
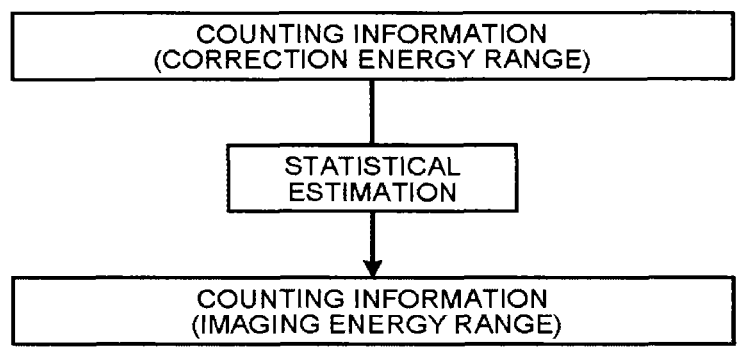

In a third embodiment, a case in which counting information of an imaging energy range that is estimated by the method explained in the first embodiment or the second embodiment is corrected is explained using FIG. 11, FIG. 12, and FIG. 13. FIG. 11, FIG. 12, FIG. 13A, and FIG. 13B are diagrams for explaining the third embodiment.

The X-ray CT apparatus according to the third embodiment is configured similarly to the X-ray CT apparatus according to the first embodiment explained using FIG. 1. However, the control unit 38 according to the third embodiment controls not to discard counting information of energy ranges out of the imaging energy range for the purpose of stabilizing the quality of reconstruction images even when pileup occurs.

As described above, the detector element 131 outputs a one-pulse electric signal at incidence of an X-ray photon. When the intensity of X-rays incident to the detector element 131 is low, the incidence interval of photons is long, and therefore, discrimination of individual pulses output from the detector element 131 is possible. However, when the intensity of X-rays incident to the detector element 131 is high, the incidence interval of photons is short. When the incidence interval is short, pulses output from the detector element 131 are piled up, and individual pulses cannot be discriminated, as shown in FIG. 11. Specifically, multiple pulses piled up are virtually discriminated as a single pulse. As a result, miscounting in counting occurs, and linearity between the number of incident photons actually entered into a sensor and a counting value (the number of pulses) of pulses that are output by the detector element 131 is lost. That is, the number of pulses is counted less than the number of photons as the intensity of X-rays becomes higher. In addition, because multiple pulses piled up are virtually discriminated as a single pulse, the energy value to be measured is to be high.

An energy spectrum indicated by a solid line in FIG. 12 is an example of an energy spectrum state in which no pileup has occurred. On the other hand, an energy spectrum indicated by a dotted line in FIG. 12 is an example of an energy spectrum in a state in which pileup has occurred under the same X-ray irradiation condition. Because of the occurrence of pileup, the energy spectrum indicated by the dotted line in FIG. 12 is shifted overall toward a direction in which the energy value increases (rightward direction in the figure) compared to the energy spectrum indicated by the solid line in FIG. 12. Moreover, because of the occurrence of pileup, in the energy spectrum indicated by the dotted line in FIG. 12, the peak becomes wider and the peak value becomes lower compared to the energy spectrum indicated by the solid line in FIG. 12.

In other words, the maximum energy value observed in the energy spectrum indicated by the dotted line in FIG. 12 is larger than the upper limit threshold of the energy range that is estimated by the method explained in the first embodiment and the second embodiment. The minimum energy value observed in the energy spectrum indicated by the dotted line in FIG. 12 approximately coincides with the lower limit threshold of the energy range that is estimated by the method explained in the first embodiment and the second embodiment.

In the third embodiment, in the energy spectrum indicated by the dotted line in FIG. 12, an energy range (refer to an elliptic circle in the figure), which has energy larger than the upper limit threshold of the imaging energy range, is focused. In the counting information of this energy range, information about pulses counted in a piled-up state is included. Therefore, by using the counting information of this energy range, counting information of the imaging energy range in which an error has occurred in the energy value and the counting value due to pileup can be statistically corrected (pileup correction).

Accordingly, the image reconstructing unit 36 according to the third embodiment reconstructs X-ray CT image data using counting information that is obtained by correcting counting information that is associated with an energy value within the energy range to be used for imaging based on counting information that is associated with an energy value out of the energy range, by the control of the control unit 38 that has estimated the energy range to be used for imaging. Specifically, the control unit 38 according to the third embodiment sets a certain range from the upper limit threshold to a certain energy value in counting information that is collected in imaging of the subject P. This certain range is to be a correction energy range. Suppose that the imaging energy range estimated by the method explained in the first embodiment is "20 keV to 80 keV" as shown in FIG. 13A, for example. In this case, the control unit 38 sets, for example, the value "160 keV", which is twice as much as the upper limit threshold "80 keV", as the certain energy value described above. Thus, the control unit 38 sets the correction energy range to "80 keV to 160 keV".

The collecting unit 14 transmits the counting information in the imaging energy range (20 keV to 80 keV) and the counting information in the correction energy range (80 keV to 160 keV) to the control unit 38 through, for example, the preprocessing unit 34, by the control of the control unit 38. Alternatively, the collecting unit 14 transmits the counting information in an expanded energy range (20 keV to 160 keV) to the control unit 38 through, for example, the preprocessing unit 34, by the control of the control unit 38. In this case, the control unit 38 divides the counting information of the expanded energy range (20 keV to 160 keV) into counting information of the imaging energy range and counting information of the correction energy range.

The control unit 38 then corrects the counting information in the imaging energy range using the counting information that is associated with the energy value in the correction energy range. That is, the control unit 38 corrects an error in the counting information in the imaging energy range by statistical estimation based on the counting information in the correction energy range as shown in FIG. 13B. Pileup correction by statistical estimation may be performed by the preprocessing unit 34 by the control of the control unit 38. Subsequently, the control unit 38 sends an instruction to perform the reconstruction processing using the corrected counting information to the image reconstructing unit 36.

Thus, the image reconstructing unit 36 reconstructs X-ray CT image data using projection data that is generated from the counting information in the imaging energy range that has been corrected.

The above correction processing may be performed using the imaging energy range that is estimated by the method explained in the second embodiment. Moreover, although in the above explanation, a case in which the collecting unit 14 collects only counting information in the expanded energy range has been explained, the present embodiment is also applicable to a case in which the collecting unit 14 collects counting information in an entire energy range in which counting is enabled, and the control unit 38 or the preprocessing unit 34 acquires counting information in the imaging energy range and counting information in the correction energy range from the counting information in the entire energy range. What has been explained in the first and the second embodiments is also applicable to the third embodiment except that the correction energy range and the expanded energy range are set to perform the pileup correction.

Next, the processing of the X-ray CT apparatus according to the third embodiment is explained using FIG. 14. FIG. 14 is a flowchart for explaining an example of the processing performed by the X-ray CT apparatus according to the third embodiment.

As shown in FIG. 14, the control unit 38 of the X-ray CT apparatus according to the third embodiment determines whether an imaging start request has been received from an operator (step S201). When an imaging start request has not been received (step S201: NO), the control unit 38 waits until an imaging start request is received.

On the other hand, when an imaging start request has been received (step S201: YES), the control unit 38 estimates the imaging energy range, and sets the correction energy range, to inform the collecting unit 14 (step S202). The control unit 38 then controls to perform CT scan (step S203).

The collecting unit 14 collects counting information in the imaging energy range and the correction energy range (step S204), and the control unit 38 corrects the counting information in the imaging energy range using the counting information in the correction energy range (step S205). The image reconstructing unit 36 reconstructs X-ray CT image data using the counting information in the imaging energy range that has been corrected (step S206).

The display device 32 then displays the X-ray CT image data based on the control by the control unit 38 (step S207), and the processing is ended.

As described above, in the third embodiment, the counting information in the imaging energy range in which a counting error and a measurement error derived from pileup are included can be corrected to counting information when pileup has not occurred, by statistical estimation using the counting information in the correction energy range. Therefore, in the third embodiment, even when pileup occurs, the quality of images that are acquired by the photon counting CT can be improved.

The present embodiment is applicable to a case in which the control unit 38 does not perform the pileup correction when it is judged that pileup has not occurred because the number of pieces of the counting information in the correction energy range is small. Such judgment can be performed using, for example, a threshold that is set for counting values and the like.

The respective structural elements of the respective units illustrated in the first to the third embodiments are of functional concepts, and it is not necessarily required to be configured physically as illustrated. That is, a specific form of distribution and integration of the respective units is not limited to the one illustrated, and it can be configured such that all or a part thereof is functionally or physically distributed or integrated in an arbitrary unit according to various kinds of loads or use conditions. Furthermore, all or arbitrary parts of the respective processing functions performed by the respective units can be implemented by a central processing unit (CPU) and a program that is analyzed and executed by the CPU, or can be implemented as hardware by a wired logic.

Moreover, the control method explained in the first to the third embodiments can be implemented by executing a control program prepared in advance by a computer such as a personal computer and a work station. This control program can be distributed through a network such as the Internet. Furthermore, this control program can be stored in a computer-readable recording medium such as a hard disk, a flexible disk (FD), a compact-disc read-only memory (CD-ROM), a magneto optical disk (MO), and a digital versatile disc (DVD), and can be executed by being read by a computer from the recording medium.

As explained, according to the first embodiment to the third embodiment, it is possible to reliably store image data that is useful for diagnostic imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modified examples as would fall within the scope and spirit of the inventions.

What is claimed is:

1. An X-ray CT apparatus comprising:
a detector that, upon incidence of an X-ray photon, outputs a signal enabling measurement of an energy value of the X-ray photon; and
processing circuitry configured to
estimate an energy range to be used for projection imaging and to reconstruct X-ray CT image data using counting information, and
correct the counting information based on other counting information, the counting information representing X-ray detections having energy values within the energy range, the other counting information representing X-ray detections having energy values in another energy range that is not used for projection imaging and to reconstruct X-ray CT image, and both the counting information and the other counting information being collected from individual signals output by the detector at each incidence of an X-ray photon that has been irradiated from an X-ray tube and has passed through a subject and representing respective counting values corresponding to the energy values of X-ray photons incident to the detector, wherein the processing circuitry is further configured to
perform the correcting of the counting information based on the other counting information, wherein the another energy range of the other counting information has a predetermined range that is from an upper limit threshold of the energy range to a predetermined energy value, and
perform reconstruction processing using the corrected counting information.

2. The X-ray CT apparatus according to claim 1, wherein the processing circuitry is further configured to acquire an upper-limit energy value of X-ray photons that are radiated from the X-ray tube based on a tube voltage that is supplied to the X-ray tube during imaging of the subject, and perform the estimating of the energy range to be used for projection imaging by setting the acquired upper-limit energy value as an upper limit threshold of the energy range.

3. The X-ray CT apparatus according to claim 1, wherein the processing circuitry is further configured to cause the X-ray tube to irradiate the X-ray photons to the detector in a state in which the subject is not mounted, collect energy spectrums at respective detector elements constituting the detector, and perform the estimating of the energy range to be used for projection imaging by setting a lower limit threshold of the energy range and an upper limit threshold of the energy range based on a minimum value and a maximum value of the energy values of the X-ray photons incident to the detector corresponding to non-zero counting values.

4. The X-ray CT apparatus according to claim 1, further comprising collecting circuitry configured to discriminate individual signals that are output from the detector to collect the respective counting values partitioned according to the corresponding energy values into pieces of counting information, wherein the processing circuitry is further configured to send an instruction to collect the pieces of counting information having an energy value within the energy range to the collecting circuitry.

5. The X-ray CT apparatus according to claim 1, further comprising collecting circuitry configured to discriminate individual signals that are output from the detector to collect the respective counting values partitioned according to the corresponding energy values into pieces of counting information, wherein the processing circuitry is configured to perform reconstruction processing using the pieces of counting information having an energy value within the energy range.

6. A control method comprising:

estimating, by processing circuitry, an energy range to be used for projection imaging;

correcting, by the processing circuitry, counting information based on other counting information; and reconstructing, by the processing circuitry, X-ray CT image data using the counting information that is obtained by correcting the counting information based on the other counting information, the counting information representing X-ray detections having energy values within the energy range, the other counting information representing X-ray detections having energy values in another energy range that is not used for projection imaging, and both the counting information and the other counting information being collected from individual signals output by a detector at each incidence of an X-ray photon that has been irradiated from an X-ray tube and has passed through a subject and representing respective counting values corresponding to the energy values of X-ray photons incident to the detector, and the another energy range of the other counting information having a predetermined range that is from an upper limit threshold of the energy range to a predetermined energy value.

7. An X-ray CT apparatus comprising:

a detector that, upon incidence of an X-ray photon, outputs a signal enabling measurement of an energy value of the X-ray photon; and processing circuitry configured to estimate an energy range to be used for projection imaging and to reconstruct X-ray CT image data using counting information, and correct the counting information based on other counting information, the counting information representing X-ray detections having energy values within the energy range, the other counting information representing X-ray detections having energy values in another energy range that is not used for projection imaging and to reconstruct X-ray CT image, and both the counting information and the other counting information being collected from individual signals output by the detector at each incidence of an X-ray photon that has been irradiated from an X-ray tube and has passed through a subject and representing respective counting values corresponding to the energy values of X-ray photons incident to the detector, wherein the X-ray tube irradiates the X-ray photons through a wedge, wherein the processing circuitry is further configured to acquire an absorbed energy range that is absorbed by the wedge based on a material and a shape of the wedge, and perform the estimating of the energy range to be used for projection imaging by setting an upper limit value of the absorbed energy range as a lower limit threshold of the energy range.

8. A control method comprising:

acquiring, by processing circuitry, an absorbed energy range that is absorbed by a wedge based on a material and a shape of the wedge;

estimating, by the processing circuitry, an energy range to be used for projection imaging by setting an upper limit value of the absorbed energy range as a lower limit threshold of the energy range; and reconstructing, by the processing circuitry, X-ray CT image data using counting information that is obtained by correcting the counting information based on other counting information, wherein the counting information represents X-ray detections having energy values within the energy range, the other counting information represents X-ray detections having energy values in another energy range that is not used for projection imaging, both the counting information and the other counting information are collected from individual signals output by a detector at each incidence of an X-ray photon that has been irradiated from an X-ray tube and has passed through a subject and representing respective counting values corresponding to the energy values of X-ray photons incident to the detector, and the X-ray tube irradiates the X-ray photons through the wedge.

* * * * *